(12) United States Patent
Henschel et al.

(10) Patent No.: US 11,219,776 B2
(45) Date of Patent: Jan. 11, 2022

(54) FIXING OF COMPONENTS IN THE INTERIOR OF AN IMPLANTABLE MEDICAL DEVICE BY MEANS OF A MOUNTING FRAME

(71) Applicant: BIOTRONIK SE & CO. KG, Berlin (DE)

(72) Inventors: Martin Henschel, Berlin (DE); Wiebke Neumann, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 69 days.

(21) Appl. No.: 16/537,683

(22) Filed: Aug. 12, 2019

(65) Prior Publication Data

US 2020/0078597 A1 Mar. 12, 2020

(30) Foreign Application Priority Data

Sep. 12, 2018 (EP) .................................. 18194057

(51) Int. Cl.
*A61N 1/39* (2006.01)
*A61N 1/375* (2006.01)
*A61N 1/378* (2006.01)

(52) U.S. Cl.
CPC ......... *A61N 1/3968* (2013.01); *A61N 1/3756* (2013.01); *A61N 1/3956* (2013.01); *A61N 1/378* (2013.01); *A61N 1/37512* (2017.08)

(58) Field of Classification Search
CPC .............. A61N 1/37512; A61N 1/3756; A61N 1/3758; A61N 1/378; A61N 1/3956; A61N 1/3968
See application file for complete search history.

(56) References Cited

U.S. PATENT DOCUMENTS

| | | | |
|---|---|---|---|
| 5,814,090 A | 9/1998 | Latterell et al. | |
| 5,873,899 A | 2/1999 | Stutz, Jr. et al. | |
| 6,118,652 A * | 9/2000 | Casby | A61N 1/3956 361/517 |
| 2004/0082977 A1 | 4/2004 | Engmark et al. | |
| 2015/0196867 A1* | 7/2015 | Ries | B01D 53/0407 429/9 |
| 2017/0127543 A1* | 5/2017 | Day | H05K 5/069 |

FOREIGN PATENT DOCUMENTS

WO 2015106109 A1 7/2015

* cited by examiner

*Primary Examiner* — Carl H Layno
*Assistant Examiner* — Anh-Khoa N Dinh
(74) *Attorney, Agent, or Firm* — Laurence A. Greenberg; Werner H. Stemer; Ralph E. Locher

(57) ABSTRACT

An implantable medical device has a device housing. The device housing has a first device housing shell and a second device housing shell. The device housing surrounds an interior space. The implantable medical device further has an electrical component arranged in the interior, as well as a mounting frame, which is arranged in the interior and surrounds the electrical component. The mounting frame has at least one clamping structure. The at least one clamping structure is configured to exert a force onto the electrical component in order to fix the electrical component in the interior of the device housing.

17 Claims, 5 Drawing Sheets

FIXING OF COMPONENTS IN THE INTERIOR OF AN IMPLANTABLE MEDICAL DEVICE BY MEANS OF A MOUNTING FRAME

CROSS-REFERENCE TO RELATED APPLICATION

This application claims the priority, under 35 U.S.C. § 119, of European application EP 18194057.8, filed Sep. 12, 2018; the prior application is herewith incorporated by reference in its entirety.

BACKGROUND OF THE INVENTION

Field of the Invention

The invention relates to an implantable medical device, in particular a cardioverter-defibrillator.

Implantable medical devices, in particular implants for stimulating an organ and/or for recording a physiological signal (for example implantable cardiac pacemakers, cardioverter-defibrillators (ICDs), neurostimulators, etc.), generally have a device housing, in which there is arranged at least one electrical component.

With the aid of an ICD of this kind it is possible to monitor the cardiac rhythm of an individual, wherein if irregularities are detected, in particular in the case of ventricular fibrillations, ventricular flutters or tachycardia, an electrical pulse can be emitted by the ICD to the heart, by means of which it is possible to reestablish a normal cardiac rhythm.

In particular, in order to achieve an unrestricted function of such implantable medical devices, a connection must be established between a printed circuit board/circuit and an electrical component (for example battery or capacitor) of the device, which connection remains intact even when the implantable medical device moves. In order to achieve this, the electrical component can be fixed in the implantable medical device. Here, the term "fixing" means that movement of the component relative to the device housing is prevented. In the case of "complete fixing" a movement of a component in all spatial directions is prevented. In the case of "incomplete fixing" a component can move at least in one spatial direction. Without fixing or in the case of incomplete fixing of the component, the component can move within the housing of the implantable medical device, and therefore for example said connection between the component and the printed circuit board/circuit can be interrupted or disturbed. This can result in a functional failure, whereby this might lead to an undesirable therapy failure.

The production process of an implantable medical device also includes a fixing of essential components within a mounting frame. A mounting frame is understood generally to mean an element that is designed to fix components of a device. A mounting frame is used to simplify production steps and to ensure reliable transport of mounted products and intermediate products.

In order to reduce movement of a component within the device, a mounting frame in which a component can be positioned is known in the prior art. A mounting frame of this kind can comprise what are known as ribs, with the aid of which the component can be fixed in a first plane, i.e. the movement of the component parallel to the first plane can be reduced or prevented. When positioning the component in such a mounting frame, however, the component can still move perpendicularly to the first plane. A complete fixing is therefore not achieved by a mounting frame of this kind.

Different solutions are disclosed in the prior art for fixing of the components perpendicularly to the first plane.

One solution provides an additional fixing of a component by gluing. However, a glue material used in this case is subject to an ageing process, and therefore the fixing can become less effective with increasing age of the implantable medical device. Furthermore, in the case of a fixing of this kind, the production time of the implantable medical device would be extended, since the glue material must cure before a further production step can be performed. Furthermore, constituents of the glue material could be responsible for changes to other components of the implantable medical device, in particular the printed circuit board. In particular, corrosion could occur, as a result of which the function of the printed circuit board and therefore the function of the implantable medical device could be reduced.

In accordance with the prior art, a solution is known alternatively, which comprises a pressing of the implantable medical device. Here, however, there is in some circumstances the risk of damage to the components or the risk that the housing will not be completely closed.

Another solution comprises an additional component, wherein the additional component can be used for fixing by way of compensation of a tolerance. An additional constituent can be for example an additional plastic film or an element formed from foam material. However, additional components can increase the costs of production of the implantable medical device undesirably.

Lastly, international patent disclosure WO 2015/106109, corresponding to U.S. Pat. No. 10,040,021, discloses a first frame, which has retaining elements, by means of which a second frame, which is positioned inside the first frame, can be stabilised.

SUMMARY OF THE INVENTION

On this basis, the objective of the present invention is to provide an implantable medical device which comprises an electrical component that can be securely fixed in a simple way in the interior of the device housing. Furthermore, the implantable medical device should be designed in particular such that the component can be arranged in the interior of the device housing in a simple way.

This objective is achieved by an implantable medical device having the features of independent claim. Advantageous embodiments are stated in the dependent claims and will be described hereinafter.

Accordingly, an implantable medical device is disclosed, having: a device housing which comprises a first and a second device housing shell, wherein the device housing surrounds an interior. The implantable medical device also comprises an electrical component arranged in the interior. In addition, the implantable medical device comprises a mounting frame, which is arranged in the interior and surrounds the electrical component. The mounting frame comprises at least one clamping structure, wherein the at least one clamping structure is configured to exert a force onto the electrical component in order to fix the electrical component in the interior of the device housing.

An implantable medical device will also be referred to hereinafter as an implant.

In one embodiment, the device housing and the mounting frame are configured to surround or to receive a printed circuit board and at least one electrical component, in particular two electrical components.

Particularly, the mounting frame may be formed integrally. The mounting frame may comprise a material or may be formed from a material that can compensate for tolerances of the components of the implant. The material may be an elastic material. In particular, the material may be one of the following materials: polybutylene terephthalate (PBTP, PBT), liquid crystal polymer (LCP), polyurethane (PU), acrylonitrile-butylene-styrene (ABS), polysulfone (PSU), polyether ether ketone (PEEK), polyoxymethylene (POM), etc.

The first and/or the second device housing shell may comprise for example one of the following materials or may be formed by one of the following materials: titanium or a titanium alloy (biocompatible).

The mounting frame may also be arranged in the first and/or the second device housing shell.

In one embodiment of the invention, the at least one clamping structure is designed to assume at least a first and a second state, wherein in the first state no force is exerted by the at least one clamping structure onto the electrical component, and wherein in the second state a force is exerted by the at least one clamping structure onto the electrical component in order to fix the component in the interior of the device housing.

Furthermore, the at least one clamping structure may be configured and positioned in such a way that in the first state the arrangement or mounting of the electrical component in the mounting frame is not disturbed and/or prevented by the clamping structure.

The arrangement or mounting can be implemented in particular along a mounting direction, i.e. the electrical component may be arranged in or inserted into the mounting frame along a mounting direction.

In accordance with a further embodiment of the invention, the at least one clamping structure is configured to be transferred from the first state into the second state when the electrical component is arranged in the mounting frame.

This means that no additional production step in the production of the implant is necessary in order to transfer the at least one clamping structure from the first state into the second state, since, by way of the arrangement of the electrical component in the mounting frame, the at least one clamping structure can be transferred from the first into the second state, and the electrical component can be fixed in the interior.

In an alternative embodiment, the at least one clamping structure is configured to be transferred from the first state into the second state when the device housing is closed by assembling together the first and the second device housing shell.

By closing the device housing, the at least one clamping structure can be transferred from the first state into the second state, and the electrical component can be fixed in the interior, such that the transfer from the first state into the second state is an additional result of a production step of the implant that has to be carried out anyway. This means that there is no need to perform an additional production or method step for transfer from the first state into the second state, i.e. for fixing the electrical component.

In accordance with a further embodiment of the invention, it is provided that the first device housing shell comprises a base and preferably a circumferential wall starting therefrom. It is furthermore provided in accordance with an embodiment of the invention that the second device housing shell comprises a base and preferably a circumferential wall starting therefrom.

The base of the first device housing shell may extend in or along a first plane. Similarly, the base of the second device housing shell may extend in or along a second plane.

When a device housing is closed, the first plane and the second plane may thus extend parallel to one another, i.e. the base of the first device housing shell may run parallel to the base of the second device housing shell. Each device housing shell may be formed in particular integrally.

Rounded forms of a device housing of which the housing shells do not have level planes are likewise conceivable.

The base of the first and/or the second device housing shell and of the mounting frame may be configured such that the mounting frame can be arranged in the interior on the base of the first and/or the second device housing shell. In particular, the mounting frame can be arrangeable or arranged in the first and/or the second device housing shell such that an electrical component can be arranged in the mounting frame along a mounting direction that runs perpendicularly to said base.

The at least one clamping structure may be configured to exert a force onto the electrical component, which force has at least one vector component extending perpendicularly to the base of the first or second device housing shell. This means that the electrical component can be fixed with the aid of the at least one clamping structure in particular perpendicularly to said base of the device housing.

Furthermore, it is provided in accordance with an embodiment of the implantable medical device that the at least one clamping structure is formed as a protrusion of the mounting frame, wherein the protrusion of the mounting frame in the first state of the at least one clamping structure extends perpendicularly to the base of the first device housing shell or perpendicularly to the base of the second device housing shell.

The protrusion in the first state may extend along the mounting direction, which runs perpendicularly to the base of the first or the second device housing shell (see above). The electrical component can therefore be arranged in the mounting frame easily along the mounting direction, without the at least one clamping structure or the at least one protrusion hindering and/or preventing the mounting.

It is furthermore provided in accordance with an embodiment of the invention that the protrusion of the mounting frame has a free end, wherein the protrusion of the mounting frame tapers towards this end.

It is furthermore provided in accordance with an embodiment of the invention that at least one region of the at least one clamping structure (for example of the protrusion or the rocker—see below) is deformable. By way of a deformation of this region of a clamping structure, the clamping structure in question can be transferred from its first state into its second state.

In an embodiment of the invention the at least one clamping structure or the at least one protrusion can be deformed by the closing of the device housing, i.e. by the intended connection of the two device housing shells, such that the at least one clamping structure (for example protrusion) is transferred from the first state into the second state, in which the at least one clamping structure fixes the component in the interior of the device housing.

If, when mounting, the mounting frame and the electrical component are arranged in the first device housing shell, the at least one protrusion of the mounting frame may protrude perpendicularly to the base of the first device housing shell, beyond the wall thereof. The second device housing shell may be configured in particular to press against the at least one protrusion as the second device housing shell is connected to the first device housing shell, such that the protrusion is transferred from the first state into the second state. Alternatively, the mounting frame or the component may firstly also be arranged in the second device housing shell. The fixing is then implemented by connecting the first device housing shell to the second device housing shell, in which the frame and the component are arranged.

The fact that at least one region of the clamping structure is deformable in order to transfer the clamping structure from the first state into the second state may also mean in particular that another region of the clamping structure in question may be present, which is not deformed during the transfer from the first state into the second state, that is to say in other words retains its form during the transfer.

For example, in accordance with a further embodiment of the invention it may be provided that the at least one clamping structure in the second state may be inclined in the direction of the base of the first or second device housing shell and thus presses against the electrical component in order to exert said force onto the electrical component and fix this in the interior of the device housing. The clamping structure may be inclined in the second state, for example in the direction of the base of the first device housing shell, when the mounting frame, during the mounting, is arranged initially in the first device housing shell. If the mounting frame, during the mounting, is arranged initially in the second device housing shell, the clamping structure in the second state may be inclined in the direction of the base of the second device housing shell.

In particular, the clamping structure may in turn press in the second state against the component with a force that has a vector component running perpendicularly to the base of the first or the second device housing shell, such that the clamping structure can fix the electrical component perpendicularly to the relevant base of the device housing.

The fact that the clamping structure in the second state can be inclined in the direction of the base of the first or the second device housing shell may mean in particular that the protrusion extends at an acute angle relative to the base of the first or second device housing shell. Accordingly, the spacing between the end of the protrusion and the base of the first or the second device housing shell in the second state may be smaller than in the first state.

In accordance with a further embodiment of the invention it is provided that the at least one clamping structure is designed as a rocker. Here, the rocker comprises at least a first and a second arm, wherein the first arm and the second arm protrude in different directions from a bar formed by the mounting frame.

In accordance with an embodiment of the invention, the mounting frame and the rocker may be formed integrally, i.e. may be manufactured from a single piece (for example by a shaping process, such as injection moulding). It is also conceivable to manufacture the mounting frame and the rocker separately from one another and then to connect them to one another.

In accordance with an embodiment of the invention, it can furthermore be provided that the first and the second arm protrude from the bar in a plane that extends perpendicularly to a direction of longitudinal extent of the bar and in particular perpendicularly to the base of the first or second device housing shell. The direction of longitudinal extent or longitudinal axis of the bar may run along a circumferential direction of the mounting frame in which the mounting frame extends circumferentially.

In accordance with a further embodiment of the invention, it is provided that the first arm of the rocker in the first state of the rocker extends inclined towards the base of the first or the second device housing shell and/or that the second arm of the rocker extends in the first state of the rocker perpendicularly to the base of the first or the second device housing shell.

The first arm and the second arm of the rocker/clamping structure may be arranged at an angle to one another. An angle formed accordingly between the two arms may be an obtuse angle between 90° and 175°, which in particular lies between 100° and 170°, in particular between 110° and 160°. In particular, the angle may be 150°.

In the first state of the rocker, the second arm for example may extend perpendicularly or at an angle of more than 90° to the base of the first device housing shell, such that the electrical component may be mounted along the mounting direction, i.e. may be arranged in the mounting frame arranged in the first device housing shell, without colliding with the second arm. This means that the second arm neither hampers nor prevents an arrangement of the electrical component in the mounting frame or in the interior of the device housing.

It is furthermore provided in accordance with an embodiment of the invention that the second arm of the rocker is longer than the first arm of the rocker.

It is furthermore provided in accordance with an embodiment of the invention that the at least one clamping structure or rocker in the first state may be tilted into the second state by exertion of a force onto the first arm. The clamping structure or rocker may be tilted about a tilt axis, which runs along the direction of longitudinal extent of the bar, wherein the bar is deformed as the rocker/clamping structure is tilted. In particular, it is provided that the rocker may be tilted from the first state into the second state by exertion of a force onto the first arm, wherein the force has a vector component running perpendicularly to the base of the first or the second device housing shell. In particular, the mounting frame may be designed such that the clamping structure or rocker tilts from the first state into the second state when the electrical component is arranged in the mounting frame. This means, in other words, that the force is exerted onto the first arm of the rocker via the electrical component when the component is introduced into the mounting frame provided, for example, in the first device housing shell and in doing so presses against the first arm of the rocker in the mounting direction, such that the rocker is tilted into the fixing second state, in which the second arm of the rocker presses against the component and fixes this in the interior or in the mounting frame. In the second state, the second arm of the rocker may extend relative to the base of the first device housing shell. In the second state, the first arm may extend perpendicularly or incline towards the base of the first device housing shell.

It is provided in particular in accordance with an embodiment of the invention that the second arm of the rocker in the second state of the rocker presses against the electrical component with a force that has a vector component perpendicular to the base of the first device housing shell.

In accordance with an embodiment of the invention it is furthermore provided that the mounting frame has a first and an opposite second edge. The bar may run here between a recess of the mounting frame on the first edge and an opposite recess of the mounting frame on the second edge. In other words, the bar thus may be configured as a narrowing of the mounting frame.

In principle in accordance with a further embodiment of the invention, it can be provided that the mounting frame comprises a further clamping structure or a plurality of clamping structures. Each clamping structure may be a protrusion of the mounting frame, which again may be configured in accordance with the embodiments described herein. Furthermore, each clamping structure may be a rocker as described herein. A combination of protrusions of the mounting frame and rockers is likewise conceivable.

Individual clamping structures of the plurality of clamping structures may be positioned in different positions along the circumferential direction of the mounting frame. Between a first clamping structure and a second clamping structure there may be provided a spacing which differs from a spacing between the second clamping structure and a third clamping structure. In an alternative embodiment, the spacing between each two clamping structures arranged adjacently in the circumferential direction may be equidistant.

A fixing of the electrical component by a plurality of clamping structures (for example protrusions and/or rockers) can be advantageous insofar as here the fixing force is distributed between a plurality of clamping structures or between a plurality of contact points to the electrical component. A defective functioning of an individual clamping structure can be compensated accordingly by way of one or more other clamping structures.

Furthermore, a plurality of electrical components of the implant may be easily fixed in the interior of the device housing or in the mounting frame by way of a plurality of clamping structures. In one embodiment, one clamping structure exerts a force onto an corresponding electrical component, respectively.

In accordance with an embodiment of the invention it is furthermore provided that the at least one electrical component of the implant is a battery, capacitor or a capacitor assembly (for example a capacitor stack). The battery in particular may deliver energy for the operation of the medical implant. The capacitor in particular may provide electrical pulses for producing a normal cardiac rhythm (defibrillation energy).

Other features which are considered as characteristic for the invention are set forth in the appended claims.

Although the invention is illustrated and described herein as embodied in a fixing of components in the interior of an implantable medical device by means of a mounting frame, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
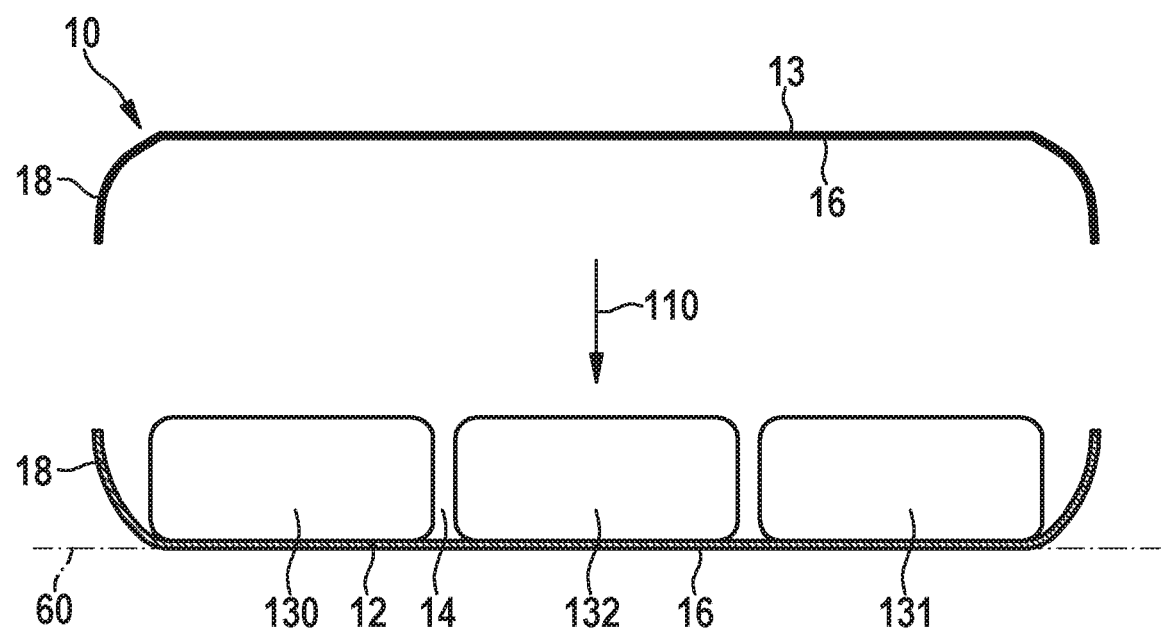
FIG. 1 is a diagrammatic, cross-sectional view of a first device housing shell with electrical components arranged therein.

Referring now to the figures of the drawings in detail and first, particularly to FIG. 1 thereof, there is shown a schematic cross-sectional view through a first device housing shell 12 of a device housing of an embodiment of an implant 1 according to the invention. The first device housing shell 12 can have a base 16 and a wall 18. The base 16 of the first device housing shell 12 can extend in a first plane 60. The wall 18 can be a circumferential wall 18 in particular.

At least one electrical component 130, 131, 132 is arranged in the first device housing shell 12. In this regard, FIG. 1 schematically shows, by way of example, a printed circuit board 132 or a circuit 132 as well as further electrical components 130, 131, which can be, for example, a battery 130 and a capacitor 131. The capacitor 131 can be provided in the form of a capacitor stack 131. The printed circuit board 132 can be positioned between the two further electrical components 130, 131.

The electrical components 130, 131, 132 can be introduced into the first device housing shell 12 along a mounting direction 110, illustrated by the arrow in FIG. 1. The mounting direction 110 preferably runs perpendicularly to the first plane 60 or the base 16 of the device housing shell 12. Hereafter, in order to form the device housing 10, a second device housing shell 13 can be connected to the first (here lower) device housing shell 12. The components 130, 131, 132 can be fixed in an interior 14 of the device housing 10 by a mounting frame 20 shown in FIG. 2. A mounting frame 20 of this kind is shown schematically in FIG. 2. FIG. 3 shows a perspective view of an embodiment of the mounting frame 20 of this kind, which here is used, for example, to position a battery 130, a capacitor 131, and a printed circuit board 132.

Figure 2:
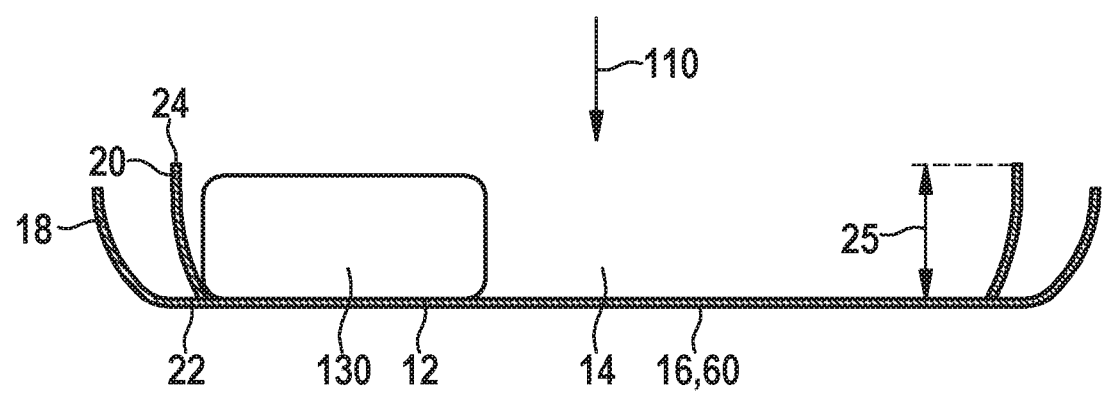
FIG. 2 is a cross-sectional view of the first device housing shell with mounting frame arranged therein and mounting direction.
Figure 3:
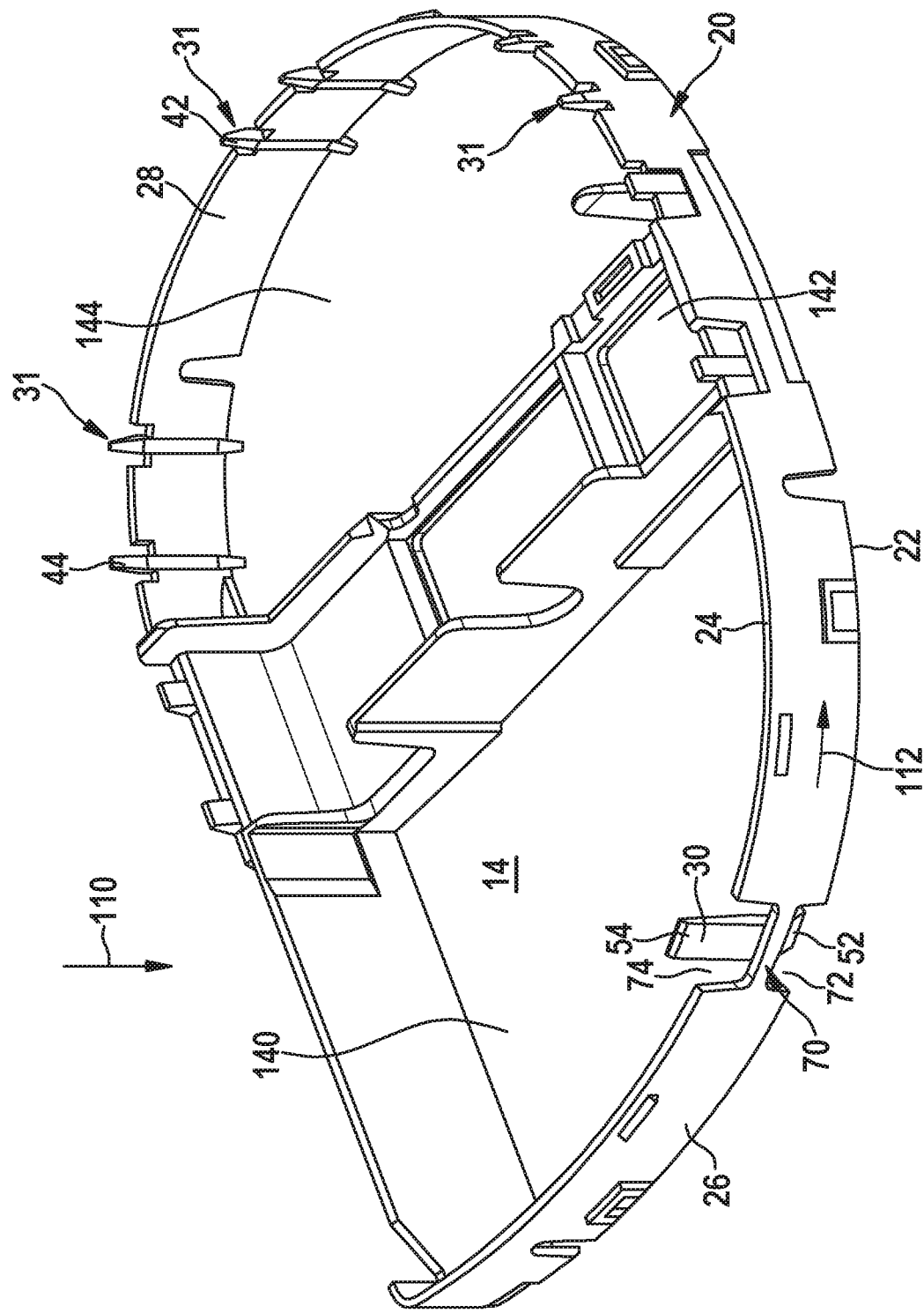
FIG. 3 is a perspective view of a mounting frame.

According to FIG. 2, the mounting frame 20 can be positioned in the interior 14 or in the first device housing shell 12 such that the mounting frame 20 can surround at least a region of the interior 14. The mounting frame 20 can comprise a first edge 22 and can rest by means of the edge 22 on the base 16 of the shell 12. The mounting frame 20 in particular comprises an opposite second edge 24, wherein the distance between the two edges 22, 24 corresponds to the height 25 of the mounting frame 20. The at least one electrical component 130, 131, 132 (only the battery 130 is shown by way of example in FIG. 2) is preferably inserted into the mounting frame 20 in the mounting direction 110, i.e. perpendicularly to the first plane 60 or the base 60.

FIG. 3 shows a perspective view of an embodiment of the mounting frame 20 according to the invention. The mounting frame 20 can surround at least a portion of the interior 14 of the device housing 10 and can be designed here in accordance with an embodiment such that it divides the interior 14 into a first region 140, a second region 142 and a third region 144. The second region 142 can be designed to surround a printed circuit board. The first and the third region 140, 144 can be designed to receive one electrical component 130, 131 each (for example in the form of a battery 130 and a capacitor 131).

In accordance with the invention it is provided that the mounting frame 20 comprises at least one or more clamping structures 30, 31. The mounting frame 20 and said clamping structures 30, 31 are furthermore shown in detail in FIGS. 4, 5A, 5B, 6A and 6B.

The at least one clamping structure 30, 31 can be designed for example in the form of a rocker 30. In an alternative embodiment the at least one clamping structure 31 can be formed by a protrusion 31 of the mounting frame 20.

In particular the mounting frame 20 in accordance with the embodiment shown in FIG. 3 can comprise a plurality of clamping structures 30, 31, more specifically in particular at least one clamping structure 30 in the form of a rocker 30 and a plurality of clamping structures 31 each in the form of a protrusion 31 of the mounting frame 20. Here, the rocker 30 can be used to fix a battery 130, whereas the protrusions 31 can be used to fix a capacitor/capacitor stack 131.

In particular the mounting frame 20 according to FIG. 3 can comprise precisely one rocker 30 and precisely six protrusions 31 of the mounting frame 20. The rocker 30 can be arranged in a first portion 26 of the mounting frame 20, which first portion can form a delimitation of the first region 140 of the interior 14, which for example can be used to receive an electrical component in the form of a battery 130. Furthermore, the protrusions 31 of the mounting frame 20 can be arranged in a second portion 28 of the mounting frame 20, which second portion can form a delimitation of the third region 144, which can be used to receive an electrical component in the form of a capacitor/capacitor stack 130. The protrusions 31 can be grouped in pairs on the second portion 28 of the frame 20.

Each protrusion 31 of the mounting frame 20 preferably has a free end 42, wherein each protrusion 31 tapers towards its end 41. Furthermore, it is provided in particular that the protrusions 31 are arranged in a recess 44 each on the second edge 24 of the mounting frame 20 or protrude in the recess 44 from the mounting frame 20. Here, the protrusions 31 extend in the mounting direction 110 in particular prior to the fixing of the component 131 in question. As is also clear from FIG. 3 (see also FIG. 4) the rocker 30 preferably comprises a first arm 52 and a second arm 54, which protrude from the mounting frame 20 in different directions. The second arm 54 is preferably longer than the first arm 52 of the rocker 30.

Figure 4:
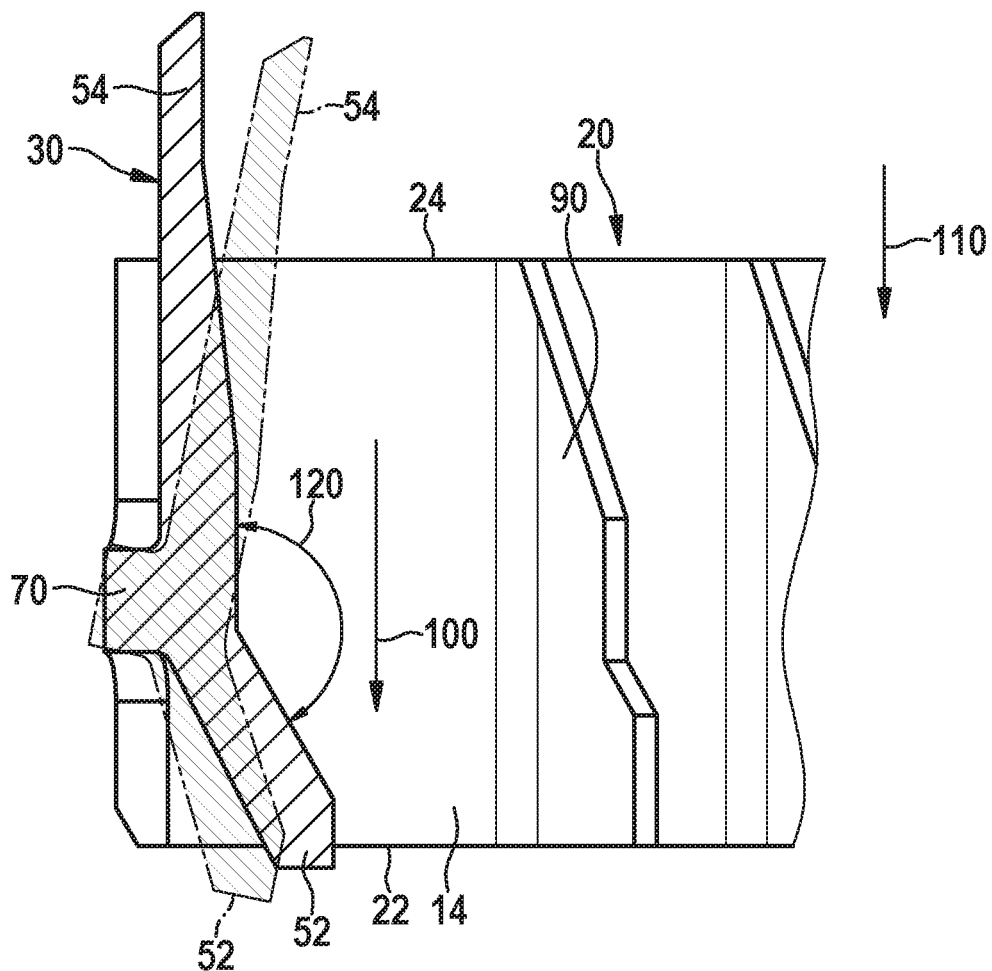
FIG. 4 is a cross-sectional view of a clamping structure in the form of a rocker.

As can be seen in particular with reference to FIGS. 3 and 4, the first and the second arm 52, 54 of the rocker 30 preferably protrude from a bar 70, which is formed by a first recess 72 in the first edge 22 and by an opposite second recesses 74 in the second edge 24 of the mounting frame 20. Here, the second recess 74 is arranged opposite the first recesses 72 in the direction of the mounting direction 110. Along the mounting direction 110 or also perpendicularly to the base 16, the spacing between the first edge 22 and the bar 70 can be smaller than the spacing between the bar 70 and the second edge 24.

The above-described clamping structures 30, 31 can each assume a first state and are designed to be transferred into a second state in order to fix the component in question 130, 131.

In this regard, FIG. 3 shows the clamping structures 30, 31 of the mounting frame 20 in the first state, wherein an arrangement of the components 130, 131 in the mounting frame 20 is possible.

In the first state, each protrusion 31 of the mounting frame 20 extends perpendicularly to the first plane 60 or the base 16 of the first device housing shell 12, on which the mounting frame 20 is arranged. Here, the mounting direction 110 runs perpendicularly to the first plane 60 or the base 16, such that each protrusion 31 extends in the mounting direction 110. The free end 42 of the protrusions 31 can project beyond the second edge 24 of the mounting frame 20 perpendicularly to the first plane 60 or the base 16.

As can also be seen from FIG. 4 the second arm 54 of the at least one rocker 30 can also extend beyond the second edge 24 of the mounting frame 20 perpendicularly to the base 16 (along the mounting direction 110).

In particular, the at least one rocker 30 can be configured such that the second arm 54 extends perpendicularly to the base 16 or the first plane 60 when the rocker is in the first state. As a result of this orientation of the rocker 30 (the same is true for the protrusions 31), the electrical component in question (here the battery 130 for example) can be arranged in the mounting frame 20 along the mounting direction 110.

Figure 5A:
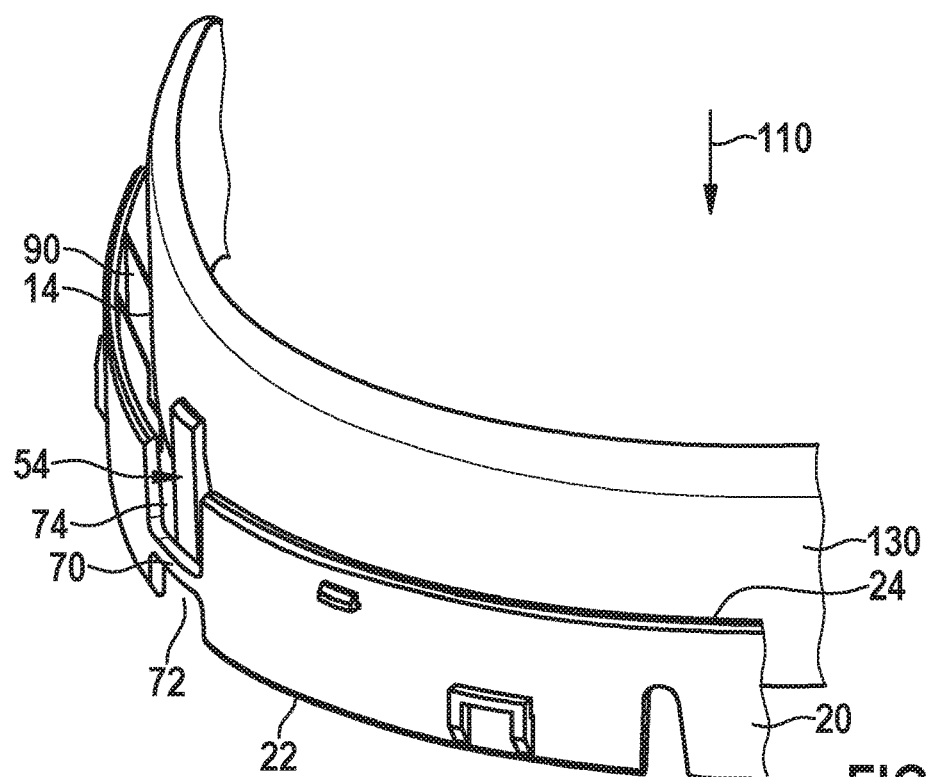
FIG. 5A is a perspective detail of the mounting frame with the rocker in the first state.
Figure 5B:
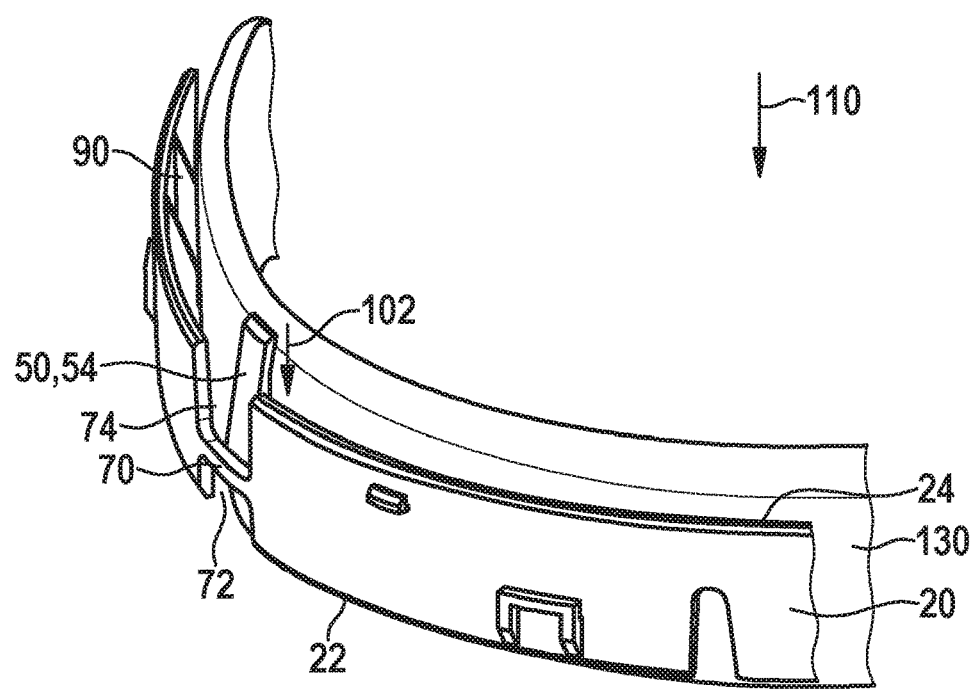
FIG. 5B is a perspective detail of the mounting frame with the rocker in the second state.
Figure 6A:
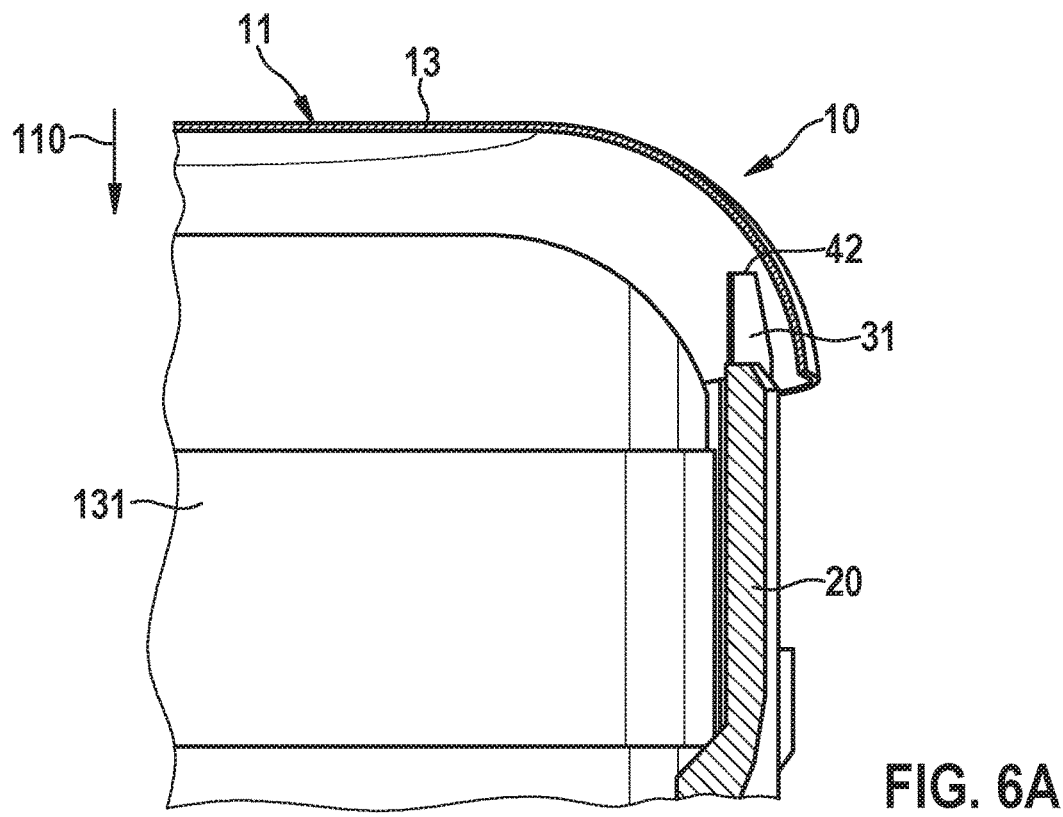
FIG. 6A is a sectional view of a detail of the mounting frame with a protrusion in the first state.
Figure 6B:
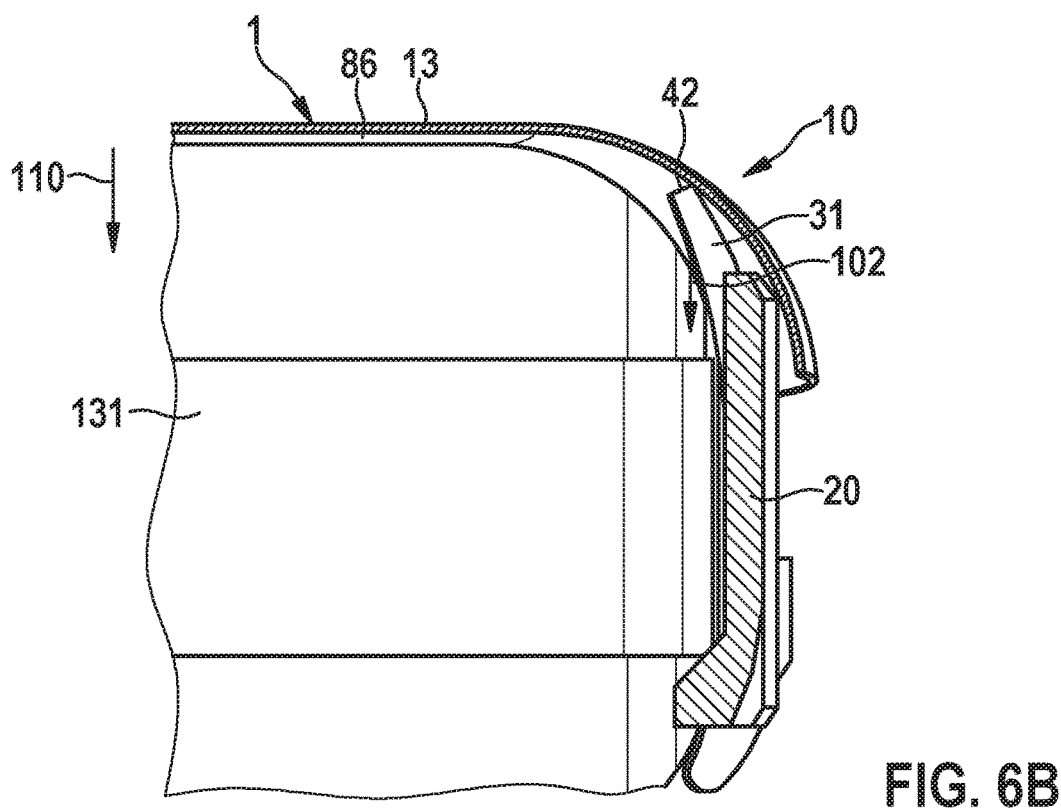
FIG. 6B is a sectional view of a detail of a mounting frame with a protrusion in the second state.

Each clamping structure 30, 31 is also designed in accordance with the invention to be transferable from the first state into a second state. This is illustrated, for example, in FIGS. 4, 5A, 5B, 6A and 6B. In FIGS. 4, 5A and 5B, the first and the second state of the at least one rocker 30 are shown. FIGS. 6A and 6B show the first and the second state for the case of a clamping structure 31 in the form of the protrusion 31.

FIG. 4, in conjunction with FIGS. 5A and 5B, shows the operating principle of the rocker 30. To this end, FIG. 4 shows a sectional view of the rocker 30 along a plane perpendicular to the direction of extent of the bar 70. The rocker 30 arranged in the first state is shown by larger hatching, whereas the rocker 30 arranged in the second state is shown by finer hatching.

The first arm 52 is preferably arranged on the bar 70 at an obtuse angle 120 to the second arm 54, wherein the first arm 52 of the rocker 30 in the first state of the rocker 30 parallel to the base 16 protrudes into the interior 14 further than the second arm 54.

As a result, for example by arranging the corresponding electrical component 130 in the mounting frame 20 (see FIG. 5A), a force 100 can be exerted onto the first arm 52 perpendicularly to the base (in the direction of the mounting direction 110), by means of which the rocker 30 is tilted, with deformation of the bar 70, from the first state into the second state, whereby the second arm 54 also presses against the component 130 and fixes this (see FIG. 5B). The rocker 30 can tilt about a tilt axis, which can extend in particular along the direction of longitudinal extent or longitudinal axis of the bar 70.

The mounting frame 20 shown in FIGS. 4, 5A and 5B can additionally comprise one or more ribs 90, with the aid of which the electrical component 130 can be fixed in the device housing 10 parallel to the first plane 60 or parallel to the base 16 of the first device housing shell 12.

FIGS. 6A and 6B each show a detailed cross-section through a device housing 10 of an implantable medical device 1 in the open state (FIG. 6A) and in the closed state (FIG. 6B) and illustrate the operating principle of a clamping structure 31 when this is provided in the form of a protrusion 31 of the mounting frame 20. FIG. 6A shows a protrusion 31 in the first state, whereas FIG. 6B shows the protrusion 31 and second state. In both cases the electrical component 130 can be arranged already in the mounting frame 20, that is to say can be located in the interior 14 of the device housing 10 of the implant 1.

In the first state (FIG. 6A) the protrusion 31 extends along the mounting direction 110. The second device housing shell 13 can now be moved towards the first device housing shell 12 in the mounting direction 110 in order to be connected to the first device housing shell. In so doing, the second device housing shell 13 presses against the end 42 of the protrusion 31 and deforms it in such a way that the protrusion presses against the electrical component and thus fixes this in the device housing 10 perpendicularly to the base 16 or the first plane 60. This is shown in FIG. 6B. The protrusion 31 can be deformed such that it bears against the electrical component 130 and exerts a force onto the electrical component 130, which force has a vector component 102 which runs along the mounting direction 110 or is oriented perpendicularly to the base 16/first plane 60.

The invention claimed is:

1. An implantable medical device, comprising:
   a device housing having a first device housing shell and a second device housing shell, wherein said device housing surrounding an interior;
   an electrical component disposed in said interior and is a battery or a capacitor; and
   a mounting frame disposed in said interior and surrounding said electrical component, said mounting frame having a bar and at least one clamping structure configured to exert a force onto said electrical component to fix said electrical component in said interior of said device housing, said at least one clamping structure being a rocker, said rocker containing at least a first arm and a second arm, wherein said first arm and said second arm protruding in different directions from said bar formed by said mounting frame, wherein said first arm extending below said bar.

2. The implantable medical device according to claim 1, wherein said at least one clamping structure is configured to assume at least a first state and a second state, wherein in the first state no force is exerted by said at least one clamping structure onto said electrical component, and in the second state a force is exerted by said at least one clamping structure onto said electrical component to fix said electrical component in said interior of said device housing.

3. The implantable medical device according to claim 2, wherein said at least one clamping structure is configured to be transferred from the first state into the second state when said electrical component is disposed in said mounting frame or when said device housing is closed by assembling together said first and second device housing shells.

4. The implantable medical device according to claim 2, wherein:
   said first device housing shell has a base and a circumferential wall starting therefrom; and/or
   said second device housing shell has a base and a circumferential wall starting therefrom.

5. The implantable medical device according to claim 4, wherein said at least one clamping structure is a protrusion of said mounting frame, wherein said protrusion of said mounting frame in the first state of said at least one clamping structure extends perpendicularly to said base of said first device housing shell or perpendicularly to said base of said second device housing shell.

6. The implantable medical device according to claim 5, wherein said protrusion of said mounting frame has an end, wherein said protrusion of said mounting frame tapers towards said end of said protrusion.

7. The implantable medical device according to claim 5, wherein said at least one clamping structure has at least one region that is deformable, such that by way of a deformation of said at least one region of said at least one clamping structure, said at least one clamping structure can be transferred from the first state into the second state.

8. The implantable medical device according to claim 5, wherein said at least one clamping structure in the second state is inclined in a direction of said base of said first device housing shell and thus presses against said electrical component to exert the force onto said electrical component.

9. The implantable medical device according to claim 1, wherein:
   said first arm in the first state extends inclined towards said base of said first device housing shell; and/or
   said second arm extends in the first state perpendicularly to said base of said first device housing shell.

10. The implantable medical device according to claim 1, wherein said second arm is longer than said first arm.

11. The implantable medical device according to claim 1, wherein said at least one clamping structure in the first state can be tilted into the second state by exerting a force onto said first arm.

12. The implantable medical device according to claim 1, wherein said mounting frame has a first edge with a recess formed therein and an opposite second edge with an opposite recess formed therein, wherein said bar runs between said recess of said mounting frame on said first edge and said opposite recess of said mounting frame on said second edge.

13. The implantable medical device according to claim 1, wherein said mounting frame has a further clamping structure, said further clamping structure is:
   a further protrusion of said mounting frame; or
   a further rocker.

14. The implantable medical device according to claim 13, wherein said further rocker has at least a first arm and a second arm.

15. The implantable medical device according to claim 14, wherein:
   said mounting frame has a further bar; and
   said at least first and second arms protrude in different directions from said further bar formed by said mounting frame.

16. The implantable medical device according to claim 1, wherein said first arm extends below said mounting frame.

17. An implantable medical device, comprising:
   a device housing having a first device housing shell and a second device housing shell, wherein said device housing surrounding an interior;
   an electrical component disposed in said interior and is a battery or a capacitor;
   a mounting frame disposed in said interior and surrounding said electrical component, said mounting frame having a bar and at least one clamping structure configured to exert a force onto said electrical component to fix said electrical component in said interior of said device housing, said at least one clamping structure being a rocker, said rocker containing at least a first arm and a second arm, wherein said first arm and said second arm protruding in different directions from said bar formed by said mounting frame; and
   said mounting frame having a first edge with a recess formed therein and an opposite second edge with an opposite recess formed therein, wherein said bar runs between said recess of said mounting frame on said first edge and said opposite recess of said mounting frame on said second edge.

* * * * *